(12) United States Patent
Tran et al.

(10) Patent No.: US 12,121,676 B2
(45) Date of Patent: Oct. 22, 2024

(54) STEERABLE CATHETER WITH MULTIPLE PULL WIRES

(71) Applicant: Edwards Lifesciences Corporation, Irvine, CA (US)

(72) Inventors: Tri D. Tran, Fountain Valley, CA (US); Sean Chow, Tustin, CA (US); Ronaldo C. Cayabyab, Mission Viejo, CA (US)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 929 days.

(21) Appl. No.: 17/026,644

(22) Filed: Sep. 21, 2020

(65) Prior Publication Data

US 2021/0001090 A1 Jan. 7, 2021

Related U.S. Application Data

(62) Division of application No. 16/128,294, filed on Sep. 11, 2018, now Pat. No. 10,792,467, which is a
(Continued)

(51) Int. Cl.
| | | |
|---|---|---|
| *A61M 25/01* | (2006.01) | |
| *A61F 2/24* | (2006.01) | |
| *A61M 25/00* | (2006.01) | |

(52) U.S. Cl.
CPC ....... *A61M 25/0147* (2013.01); *A61F 2/2436* (2013.01); *A61M 25/0071* (2013.01);
(Continued)

(58) Field of Classification Search
CPC .......... A61M 25/0071; A61M 25/0133; A61M 25/0147; A61M 2025/015;
(Continued)

(56) References Cited

U.S. PATENT DOCUMENTS

| | | |
|---|---|---|
| 4,035,849 A | 7/1977 | Angell et al. |
| 4,592,340 A | 6/1986 | Boyles |

(Continued)

FOREIGN PATENT DOCUMENTS

| | | |
|---|---|---|
| DE | 19532846 A1 | 3/1997 |
| DE | 19907646 A1 | 8/2000 |

(Continued)

OTHER PUBLICATIONS

International Search Report from corresponding PCT case No. PCT/US2015/063481 dated Apr. 14, 2016.

*Primary Examiner* — Wade Miles
(74) *Attorney, Agent, or Firm* — Klarquist Sparkman, LLP; Joel B. German

(57) ABSTRACT

In one representative embodiment, a steerable catheter device comprises a shaft comprising a proximal portion and a distal portion, and first and second pull wires having respective proximal portions and respective distal portions. The proximal portions of the first and second pull wires extend through the proximal portion of the shaft in close proximity to each other. The distal portions of the first and second pull wires extend through the distal portion of the shaft in close proximity to each other over a first distance defining a primary flexing section, diverge away from each other over a second distance, and then extend parallel to each other at angularly spaced locations over a third distance defining a secondary flexing section.

19 Claims, 8 Drawing Sheets

Related U.S. Application Data division of application No. 14/949,707, filed on Nov. 23, 2015, now Pat. No. 10,076,638.

(60) Provisional application No. 62/088,449, filed on Dec. 5, 2014.

(52) U.S. Cl.
CPC ....... *A61M 25/0136* (2013.01); *A61F 2/2427* (2013.01); *A61M 2025/0161* (2013.01)

(58) Field of Classification Search
CPC .......... A61M 2025/0161; A61F 2/2427; A61F 2/2436; A61F 2/962; A61F 2/966
See application file for complete search history.

(56) References Cited

U.S. PATENT DOCUMENTS

| | | |
|---|---|---|
| 4,994,077 A | 2/1991 | Dobben |
| 5,059,177 A | 10/1991 | Towne et al. |
| 5,411,552 A | 5/1995 | Andersen et al. |
| 5,554,185 A | 9/1996 | Block et al. |
| 5,591,195 A | 1/1997 | Taheri et al. |
| 5,599,305 A | 2/1997 | Hermann et al. |
| 5,639,274 A | 6/1997 | Fischell et al. |
| 5,728,068 A | 3/1998 | Leone et al. |
| 5,840,081 A | 11/1998 | Andersen et al. |
| 5,944,690 A | 8/1999 | Falwell et al. |
| 5,968,068 A | 10/1999 | Dehdashtian et al. |
| 6,168,614 B1 | 1/2001 | Andersen et al. |
| 6,217,585 B1 | 4/2001 | Houser et al. |
| 6,379,372 B1 | 4/2002 | Dehdashtian et al. |
| 6,454,799 B1 | 9/2002 | Schreck |
| 6,458,153 B1 | 10/2002 | Bailey et al. |
| 6,461,382 B1 | 10/2002 | Cao |
| 6,527,979 B2 | 3/2003 | Constantz |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 7,018,406 B2 | 3/2006 | Seguin et al. |
| 7,018,408 B2 | 3/2006 | Bailey et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,510,575 B2 | 3/2009 | Spenser et al. |
| 7,585,321 B2 | 9/2009 | Cribier |
| 7,618,446 B2 | 11/2009 | Andersen et al. |
| 7,785,366 B2 | 8/2010 | Maurer et al. |
| 8,029,556 B2 | 10/2011 | Rowe |
| 8,167,932 B2 | 5/2012 | Bourang |
| 8,449,606 B2 | 5/2013 | Eliasen et al. |
| 8,880,147 B2 | 11/2014 | Tegg et al. |
| 2002/0032481 A1 | 3/2002 | Gabbay |
| 2003/0050694 A1 | 3/2003 | Yang et al. |
| 2003/0130712 A1 | 7/2003 | Smits et al. |
| 2004/0122360 A1 | 6/2004 | Waldhauser et al. |
| 2004/0133263 A1 | 7/2004 | Dusbabek et al. |
| 2004/0186565 A1 | 9/2004 | Schreck |
| 2004/0260389 A1 | 12/2004 | Case et al. |
| 2005/0096736 A1 | 5/2005 | Osse et al. |
| 2005/0203614 A1 | 9/2005 | Forster et al. |
| 2005/0203617 A1 | 9/2005 | Forster et al. |
| 2006/0025857 A1 | 2/2006 | Bergheim et al. |
| 2007/0005131 A1 | 1/2007 | Taylor |
| 2007/0066878 A1 | 3/2007 | Worley et al. |
| 2007/0149995 A1 | 6/2007 | Quinn et al. |
| 2007/0203575 A1 | 8/2007 | Forster et al. |
| 2007/0265700 A1 | 11/2007 | Eliasen et al. |
| 2007/0282358 A1 | 12/2007 | Remiszewski et al. |
| 2008/0125853 A1 | 5/2008 | Bailey et al. |
| 2008/0262301 A1* | 10/2008 | Gibbons ........... A61M 25/0147 600/114 |
| 2008/0294230 A1 | 11/2008 | Parker |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0319037 A1 | 12/2009 | Rowe et al. |
| 2010/0049313 A1 | 2/2010 | Alon et al. |
| 2010/0198347 A1 | 8/2010 | Zakay et al. |
| 2011/0015729 A1 | 1/2011 | Jimenez et al. |
| 2011/0196186 A1 | 8/2011 | Bonan et al. |
| 2011/0270173 A1* | 11/2011 | Gibson ............. A61M 25/0108 604/95.04 |
| 2012/0123529 A1 | 5/2012 | Levi et al. |
| 2013/0231567 A1 | 9/2013 | Barthe et al. |
| 2013/0231657 A1 | 9/2013 | Datta et al. |
| 2013/0317598 A1 | 11/2013 | Rowe et al. |

FOREIGN PATENT DOCUMENTS

| | | |
|---|---|---|
| EP | 0592410 B1 | 10/1995 |
| EP | 0850607 A1 | 7/1998 |
| EP | 1796597 A2 | 6/2007 |
| FR | 2815844 A1 | 5/2002 |
| JP | 2001516257 A | 9/2001 |
| JP | 2014087386 A | 5/2014 |
| WO | 9117720 A1 | 11/1991 |
| WO | 9829057 A1 | 7/1998 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 03047468 A1 | 6/2003 |
| WO | 2005084595 A1 | 9/2005 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2010121076 A2 | 10/2010 |

\* cited by examiner

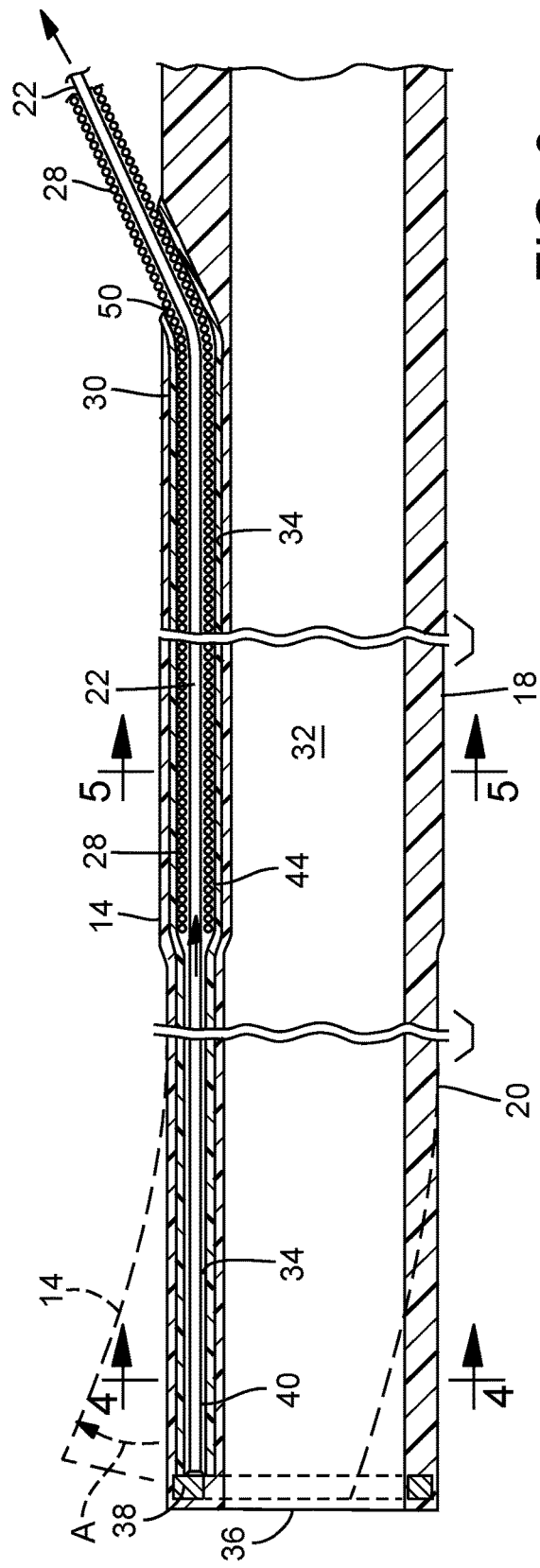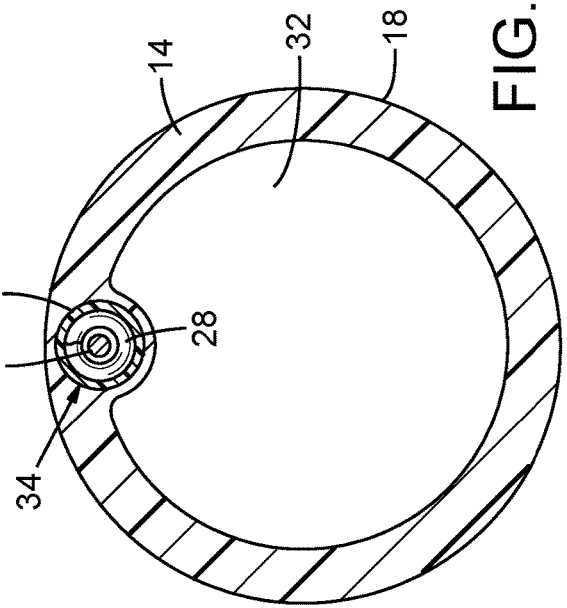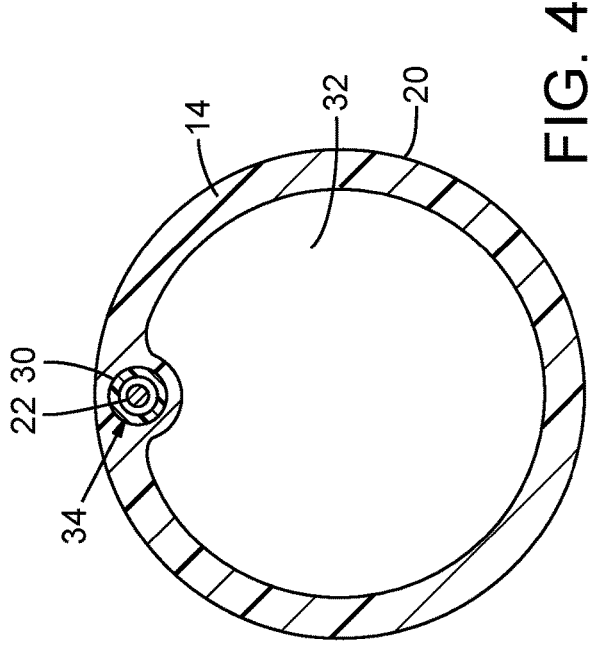

STEERABLE CATHETER WITH MULTIPLE PULL WIRES

CROSS-REFEFERENCE TO RELATED APPLICATIONS

The present application is a divisional of U.S. application Ser. No. 16/128,294, filed Sep. 11, 2018, which is a divisional of U.S. application Ser. No. 14/949,707, filed Nov. 23, 2015, now U.S. Pat. No. 10,076,638, which claims the benefit of U.S. Provisional Application No. 62/088,449, filed Dec. 5, 2014, all of which applications are incorporated herein by reference.

FIELD

The present application pertains to embodiments of steerable endovascular delivery devices.

BACKGROUND

Endovascular delivery devices are used in various procedures to deliver prosthetic medical devices or instruments to locations inside the body that are not readily accessible by surgery or where access without surgery is desirable. Access to a target location inside the body can be achieved by inserting and guiding the delivery device through a pathway or lumen in the body, including, but not limited to, a blood vessel, an esophagus, a trachea, any portion of the gastrointestinal tract, a lymphatic vessel, to name a few. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size such as by inflating a balloon on which the prosthetic valve is mounted, or by deploying the prosthetic valve from a sheath of the delivery device so that the prosthetic valve can self-expand to its functional size.

The usefulness of delivery devices is largely limited by the ability of the device to successfully navigate through small vessels and around tight bends in the vasculature, such as around the aortic arch. Various techniques have been employed to adjust the curvature of a section of a delivery device to help "steer" the valve through bends in the vasculature. Typically, a delivery device employs a pull wire having a distal end fixedly secured to the steerable section and a proximal end operatively connected to an adjustment knob located on a handle of the delivery device outside the body. The pull wire is typically disposed in a pull-wire lumen that extends longitudinally in or adjacent to a wall of the delivery device, for example, a sheath or catheter. Adjusting the adjustment knob, for example, rotating the knob, applies a pulling force on the pull wire, which in turn causes the steerable section to bend.

A drawback of this design is that the delivery device suffers from a phenomenon known as "whipping" when the device is torqued or rotated relative to its central longitudinal axis, for example to adjust the rotational position of the distal end portion of the delivery device, while the delivery device is disposed in a curved anatomical pathway, for example, a blood vessel, while the steerable section is deflected to match the curvature of the anatomical pathway. In the deflected configuration, the pull wire and pull-wire lumen adopt a low-energy configuration along an inside of the curved section of the delivery device. The deflected portion of the delivery device resists rotation around the longitudinal axis because such rotation would move the pull wire away from the inside of the curve. In many cases, this resistance makes rotation impossible as a practical matter. "Whipping" occurs when the user successfully rotates the delivery device: as the handle is rotated, the curved section initially resists, then, as the user continues to rotate the handle, suddenly rotates a full 360° from the initial low-energy configuration to a final (equivalent) low energy configuration. Some prior art devices utilize multiple pull wires or tensioning members to effect positioning of the steerable section in more than one flexing plane relative to the central axis of the device; however, these devices are complicated, and like single pull-wire devices, suffer from "whipping" when rotated. Thus, a need exists for a delivery device with improved torqueability and steerability.

SUMMARY

Disclosed herein are steerable catheter devices and related methods, which can be used to deliver a medical device, tools, agents, or other therapy to a location within a body of a subject. In some implementations, the steerable catheter devices can be used to deliver a medical device through the vasculature, such as to a heart of the subject. These devices may comprise one or more eccentrically positioned pull wires configured to cause a shaft to curve in a given direction, and/or to cause the shaft to straighten. The disclosed devices can further comprise a flexible, axially non-compressible pull-wire sleeve that extends co-axially over at least a portion of the pull wire, with the pull-wire sleeve free-floating within a pull-wire lumen. The pull-wire sleeve is effective to reduce or eliminate disequilibrium caused by torqueing the shaft while in a contoured configuration and under the pulling force of the pull wire, thereby enhancing the steerability and torqueability of the catheter device.

In one representative embodiment, a steerable catheter device comprises a shaft comprising a proximal portion, a distal portion, and a pull-wire lumen that extends at least partially through the proximal and distal portions. A pull wire extends through the pull-wire lumen and has a proximal end portion and a distal end portion, wherein the distal end portion of pull wire is fixed to the distal portion of the shaft. An adjustment mechanism is operatively connected to the proximal end portion of the pull wire and configured to increase and decrease tension in the pull wire to adjust the curvature of the distal portion of the shaft. An axially non-compressible pull-wire sleeve extends co-axially through the pull-wire lumen and over the pull wire.

In another representative embodiment, a method comprises providing a catheter device having a shaft, a pull wire extending through the shaft, and an axially non-compressible pull-wire sleeve. The pull wire extends at least partially through the pull-wire sleeve, the pull wire and the pull-wire sleeve are radially offset from a central axis of the shaft, and the shaft comprises a proximal portion and a distal portion. The method further comprises inserting the catheter device into the body of a patient and applying tension to the pull wire to adjust the curvature of the distal portion of the shaft.

In another representative embodiment, a steerable catheter device comprises a shaft having a proximal portion and a distal portion, and first and second pull wires. The first and second pull wires have respective proximal portions and respective distal portions. The proximal portions of the first and second pull wires extend through the proximal portion of the shaft in close proximity to each other. The distal end portions of the first and second pull wires extend through the distal portion of the shaft in close proximity to each other over a first distance defining a primary flexing section, diverge away from each other over a second distance, and then extend parallel to each other at angularly spaced locations over a third distance defining a secondary flexing section. Tension applied to the first pull wire and/or the second pull wire is effective to flex the distal portion away from the central axis of the shaft, wherein the direction of flexion is determined by the relative tensions in the pull wires.

The foregoing and other objects, features, and advantages of the invention will become more apparent from the following detailed description, which proceeds with reference to the accompanying figures.

BRIEF DESCRIPTION OF THE DRAWINGS

FIG. 3 is a longitudinal cross-sectional view of the catheter device of FIG. 1.

FIG. 4 is a cross-sectional view of the catheter device of FIG. 1, taken along line 4-4 of FIG. 3.

FIG. 5 is another cross-sectional view of the catheter device of FIG. 1, taken along line 5-5 of FIG. 3.

DETAILED DESCRIPTION

Disclosed herein are steerable catheter devices and related methods, which can be used to deliver a medical device, tools, agents, or other therapy to a location within the body of a subject. Examples of procedures in which the steerable catheters are useful include neurological, urological, gynecological, fertility (e.g., in vitro fertilization, artificial insemination), laparoscopic, arthroscopic, transesophageal, transvaginal, transvesical, transrectal, and procedures including access in any body duct or cavity. Particular examples include placing implants, including stents, grafts, embolic coils, and the like; positioning imaging devices and/or components thereof, including ultrasound transducers; and positioning energy sources, for example, for performing lithotripsy, RF sources, ultrasound emitters, electromagnetic sources, laser sources, thermal sources, and the like. In some embodiments, the steerable catheter device is a steerable balloon catheter, comprising one or more balloons at or near a distal end portion thereof. In some implementations, the steerable catheter devices can be used to deliver a medical device through the vasculature, such as to a heart of the subject. These devices may comprise one or more eccentrically positioned pull wires configured to cause a shaft to curve in a given direction, or to straighten. The disclosed devices can further comprise a flexible, axially non-compressible pull-wire sleeve that extends co-axially over at least a portion of the pull wire and is free-floating within a pull-wire lumen. The pull-wire sleeve effectively reduces or eliminates disequilibrium caused by torqueing the shaft while in a contoured configuration and under the pulling force of the pull wire, thereby enhancing the steerability and torqueability of the catheter device.

Exemplary Embodiments

Figure 1:
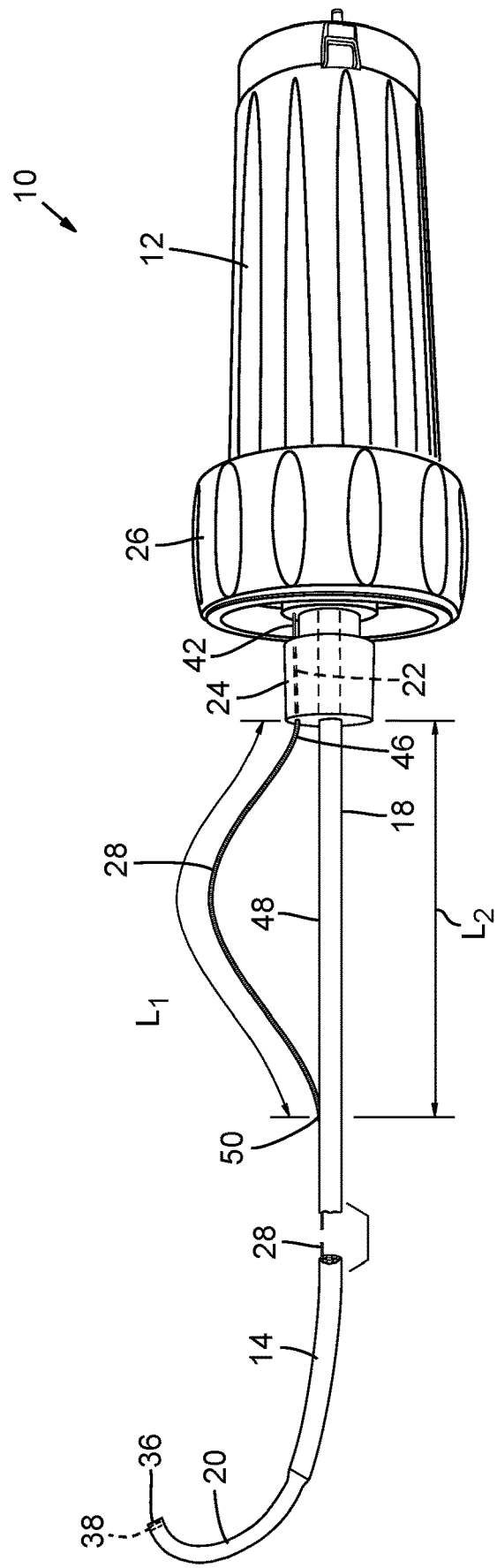
FIG. 1 is a side view of a catheter device, according to one embodiment.

Referring to FIG. 1, a catheter device 10, according to one embodiment, comprises a handle portion 12 and a shaft 14 extending distally therefrom. The shaft 14 comprises a proximal portion 18 and a distal portion 20. The curvature of the distal portion 20 of the shaft 14 can be controlled by a pull wire 22. As best shown in FIG. 3, the pull wire 22 extends through a peripheral pull-wire lumen 34 formed in a side wall of the shaft 14, and has a proximal end portion 42 operatively connected to an adjustment mechanism 26 in the form of a rotatable knob mounted on the handle 12. The adjustment mechanism 26 is configured to increase and decrease tension in the pull wire to adjust the curvature of the distal portion 20 of the shaft 14, as further described below. The distal portion 20 of the shaft can be constructed from a relatively more flexible material than the proximal portion 18 or otherwise can be constructed to be relatively more flexible than the proximal portion 20 such that the curvature of the proximal portion can remain substantially unchanged when the curvature of the distal portion is adjusted by applying tension thereto by the pull wire, as further described below. Further details of the construction of the shaft, the handle and the adjustment mechanism are described in U.S. Patent Application Publication Nos. 2013/0030519, 2009/0281619, 2008/0065011, and 2007/0005131, which are incorporated herein by reference in their entireties.

The catheter device 10 can further comprise a flexible, axially non-compressible pull-wire sleeve 28 extending co-axially over at least a portion of the length of the pull wire 22. In the illustrated embodiment, the pull-wire sleeve 28 comprises a helical coil, which desirably is a closed pitch coil without spacing between adjacent turns of the coil to avoid axial compression of the coil. The coil can be made of any suitable biocompatible metal (e.g., stainless steel, nitinol, etc.), polymer, or combination thereof. In alternative embodiments, the pull-wire sleeve 28 can have other configurations that are sufficiently flexible yet substantially axially non-compressible. For example, the pull-wire sleeve can comprise an elongated slotted tube (e.g., a metal tube) that has a plurality of axially-spaced, circumferentially extending slots formed (such as by laser cutting) along the length of the tube. In another example, the pull-wire sleeve 28 can comprise a polymeric tube reinforced with a braided metal layer, such as polyimide tube reinforced with a braided stainless steel layer. In this example, an inner polymeric layer can be secured to the inner surface of the braided layer and/or an outer polymeric layer can be secured to the outer surface of the braided layer.

Figure 1A:
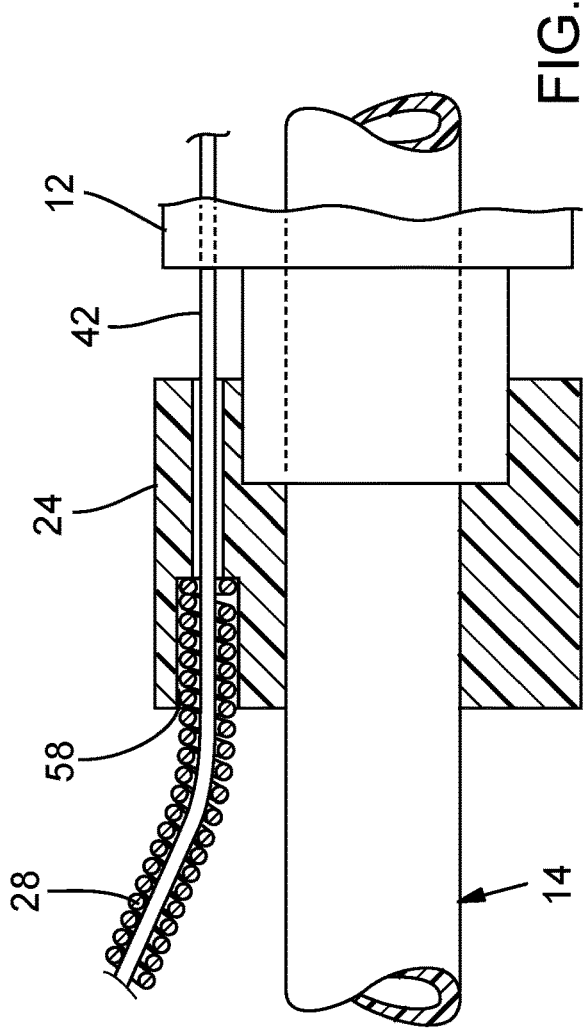
FIG. 1A is an enlarged view of a portion of the catheter device of FIG. 1, showing the connection of a pull-wire sleeve to a stop member.

Referring to FIGS. 1 and 3, the coil 28 extends through the pull-wire lumen 34 for the majority of the length of the shaft and proximate the handle 12, the coil extends outside the shaft 14 through an opening 50 in the proximal portion 18 of the shaft and terminates at a stop member 24 mounted on the shaft adjacent the handle. A length of the coil 28 extending outside of the shaft 14 is shown as $L_1$ in FIG. 1. The proximal end of the coil 28 can be fixed to the stop member 24, such as mechanically, by press-fitting, by threads, by swaging, by crimping, by clamping, by welding, or using a suitable adhesive. As shown in FIG. 1A, the proximal end of the coil 28 can extend into a bore 58 in the stop member 24, where the coil can be secured in place, as discussed above. In various other embodiments, the coil 28 can originate more proximally (proximal to the stop member 24), such as at the handle portion 12, or more distally (distal to the stop member 24).

As shown in FIG. 3, a distal end portion 40 of the pull wire 22 can be fixed relative to the shaft 14 proximate of the distal, terminal end 36 of the shaft. For example, the distal end portion 40 of the pull wire 22 can be fixed to a ring 38 that is embedded or otherwise secured to the shaft at or adjacent the distal opening of the pull-wire lumen 34. As shown in FIGS. 1 and 1A, a proximal end portion 42 of the pull wire 22 extends through the stop member 24 and into the handle 12 where it is operative connected to the adjustment knob 26. For example, the proximal end portion 42 of the pull wire can be secured to a slidable nut (not shown) inside the handle which is configured to apply and release tension on the pull wire upon rotation of the knob 26.

When tension is applied to the pull wire 22, side wall areas of the distal portion 20 of the shaft in proximity to the pull wire 22 are compressed, while side wall areas on the opposite side are tensed/stretched, thereby causing flexion of the distal portion 20 in the direction of the pull wire 22 (relative to a central axis of the distal end portion 20) (as shown in FIG. 1 and in phantom in FIG. 3). The adjustment knob 26 located on the handle 12 can be turned in one direction to apply tension to the pull wire 22, and can be turned in the opposite direction to release tension thereupon. In some embodiments, the knob 26 is turned clockwise to apply tension, while in other embodiments, counter-clockwise rotation applies the tension. In any case, when tension in the pull wire is decreased or released, the resiliency of the distal portion 20 of the shaft causes the distal portion to return to its non-flexed configuration. In its non-flexed configuration (in the absence of pull-wire forces), the distal portion 20 can be substantially straight (as shown in FIG. 3) or can be curved.

In alternative embodiments, the distal portion 20 can be curved when it is in its non-flexed configuration, and application of tension by the pull wire causes the distal portion 20 to straighten while release of tension allows the distal portion to return to its pre-curved, non-flexed configuration. In such embodiments, the pull wire 22 extends through a pull-wire lumen that is offset from the central axis of the shaft toward the outer, convex curved portion of the shaft such that the pull wire applies a tensile force to the inner, concave curved portion of the shaft and a compressive force to the outer, convex curved portion of the shaft. In other embodiments, the pull-wire lumen extends longitudinally at a location other than the inside or outside of a pre-curved catheter.

As shown in FIGS. 3-5, the shaft 14 can comprise a central lumen 32 that extends the length of the shaft. The central lumen 32, the diameter of which can be significantly larger than the diameter of the pull-wire lumen 34, can be used to transport one or more of a medical device, tools, medicament, or other substance. In some embodiments, the central lumen 32 is used to transport a prosthetic heart valve. A low-friction and/or flexible liner 30 can cover the inner surface of the pull-wire lumen 34, and can comprise polytetrafluoroethylene (PTFE), ultra-high-molecular-weight polyethylene (UHMWPE), or another suitable material. The liner 30 can be sufficiently flexible and/or distensible to accommodate insertion of the coil 28 into the pull-wire lumen 34.

As shown in FIG. 3, in the illustrated embodiment, the coil 28 extends through the pull-wire lumen 34 co-axially over the pull wire 22 and terminates short of the steerable distal portion 20 of the shaft. A distal end portion 44 of the coil can be fixed to the inner liner 30 by any suitable method, such as with a suitable adhesive.

As noted above, a portion of the coil 28 and the pull wire 22 proximate the handle 12 extend outside of the shaft. Although this portion is illustrated distal from the handle 12 in the illustrated embodiment, in other embodiments, the portion of the coil and pull wire outside of the shaft is enclosed by the handle. The section of the shaft 14 that does not contain the coil and the pull wire can be referred to as a "bypassed segment" 48 of the shaft 14 (FIG. 1). This bypassed segment 48 can have a length $L_2$ extending from a first location where the coil 28 extends outwardly from the shaft 14 at opening 50 to a second location at the proximal end of the coil 28 (at the distal face of the stop member 24 in the illustrated embodiment). In various embodiments, $L_2$ can be relatively small in comparison to the length of the shaft 14. In various embodiments, the overall length of the shaft can be about 91 cm to about 152 cm, and the length of the bypassed segment 48 $L_2$ desirably is in the range of about 5 cm to about 10 cm. In some cases, the ratio of $L_2$ to the overall length of the shaft 14 is less than about $1/20$, less than about $1/15$, or less than about $1/10$. As can be seen in FIG. 1, the length $L_1$ of the coil 28 extending outside of the shaft is greater than the length $L_2$ of the bypassed segment 48 of the shaft, the significance of which is explained below. When no tension is being applied to the pull wire 22 and the shaft 14 is in its non-flexed or relaxed configuration, the length $L_1$ of the portion of the coil 28 extending outside of the shaft 14 can be at least about 5-10 mm greater than the length $L_2$.

As noted above, the distal end portion 44 of the coil 28 can be fixed relative to the shaft 14 (FIG. 3) and the proximal end portion 46 can be fixed relative to the shaft 14 (via the stop member 24 in the illustrated embodiment in the embodiment illustrated in FIGS. 1 and 1A), while the section of the coil 28 extending outside of the shaft introduces an amount of slack in the coil. Between the proximal end portion 46 and the distal end portion 44, the coil 28 desirably is unattached or unsecured to the inner surface of the pull-wire lumen 34, the shaft, or any other portion of the delivery device. This allows the coil to "free float" or freely slide relative to the pull-wire lumen 34, permitting the coil to accommodate relative movement between the pull-wire lumen and the coil as the shaft 14 is advanced through and/or rotated within a tortuous path, for example, when rotated from an inside of a curve to an outside of the curve, without changing the tension on the pull wire. In this manner, the tensile force of the pull wire 22 can be transferred to the distal portion 20 of the shaft 14 while the coil 28 takes up the tensile force of the pull wire 22 along the proximal portion 18 of the shaft so as to prevent or minimize the application of a non-concentric tensile force to the proximal portion 18 of the shaft 14. Advantageously, this prevents the so-called "whipping" phenomenon of the shaft when a torqueing force is applied to shaft, allowing the distal end of the shaft to be rotated relative to the central longitudinal axis to any position through 360 degrees in three-dimensional space.

Another important advantage of the catheter device 10 is that it only requires a single pull wire to orient the steerable distal portion at any position in three-dimensional space within a body lumen, whereas many prior art devices utilize multiple pull wires or tensioning members to effect positioning of the distal portion in more than one flexing plane. As can be appreciated, utilizing only a single pull wire greatly simplifies the manufacture as well as use of the catheter device.

FIGS. 2A-2D illustrates the use of the catheter device 10 shown in FIG. 1. In FIGS. 2A-2D, the catheter device 10 includes an outer shaft 52 that extends over the shaft 14, which is an inner shaft in this embodiment. The outer shaft 52 can have a pre-set curvature, which in the illustrated example curves in the x-y plane. Alternatively, the outer shaft 52 can have a steerable distal end portion, the curvature of which can be adjusted using known techniques (e.g., a pull wire and adjustment knob, such as disclosed in any of U.S. Patent Application Publication Nos. 2013/0030519, 2009/0281619, 2008/0065011, and 2007/0005131, the disclosures which are incorporated by reference in their entireties). In cases where the outer shaft 52 is steerable, the handle 12 can include an additional adjustment knob to control the curvature of the shaft 52, or a separate handle and respective adjustment knob can be provided.

Figure 2A:
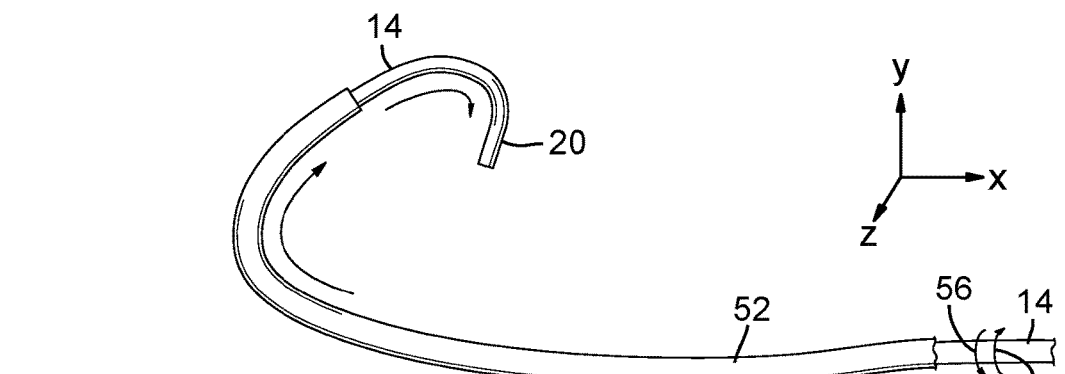
FIG. 2A is a side view of a catheter device of FIG. 1 shown with a curved outer shaft and with a steerable distal tip portion of an inner shaft curling inwards in the same plane (x-y plane) as a curved outer shaft of the assembly.
Figure 2B:
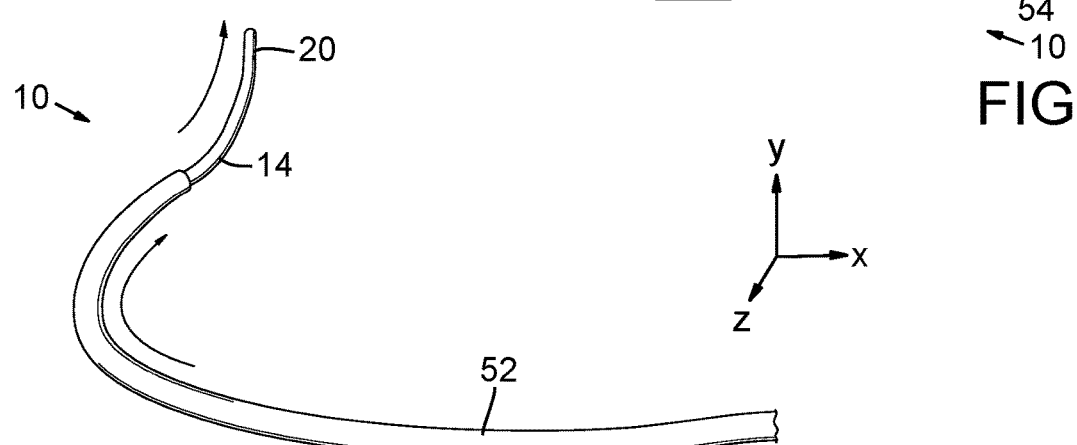
FIG. 2B is a side view of the catheter device of FIG. 2A, with a distal tip portion of an inner shaft of the assembly extending in a direction orthogonal to the plane of the outer shaft (into the page as shown).
Figure 2C:
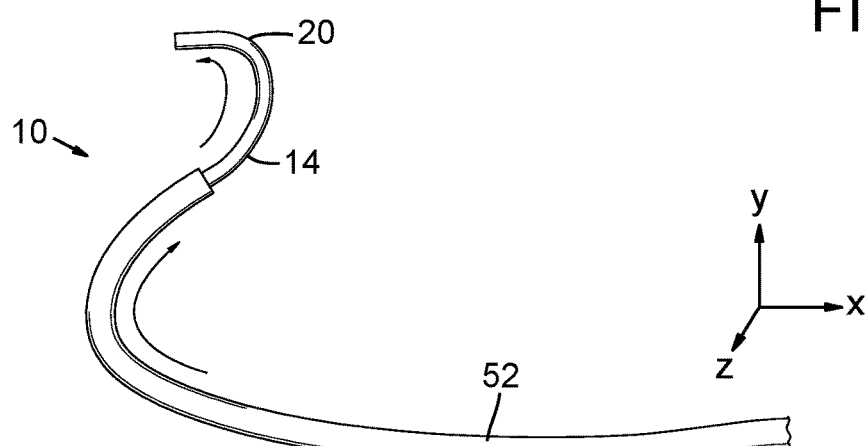
FIG. 2C is a side view of the catheter device of FIG. 2A, with a distal tip portion of an inner shaft of the assembly flexing in an opposite direction from the outer shaft but in the same plane (x-y plane) as the outer shaft.
Figure 2D:
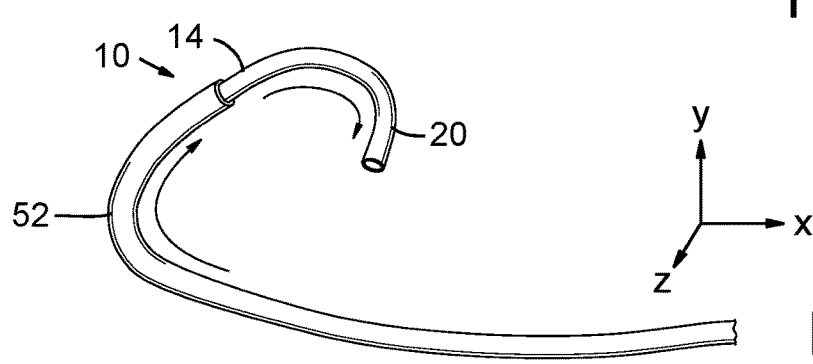
FIG. 2D is side view of the catheter device of FIG. 2A, with a distal tip portion of an inner shaft of the assembly extending in a direction orthogonal to the plane of the outer shaft (out of the page as shown).

The curvature of the inner shaft 14 can be controlled independently of the curvature of the outer shaft 52. Furthermore, the inner shaft 14 can be freely rotated through 360 degrees relative to the outer shaft 52 (in the directions indicated by arrows 54, 56) while the both the inner and outer shafts are in their curved or deflected configurations, as illustrated in the drawings. In FIG. 2A, for example, the distal end portion 20 of the inner shaft 14 is curved and lies in the x-y plane with the outer shaft 52, indicating that the inner shaft 14 has not been rotated or torqued relative to the outer shaft 52 (referred to as zero-degree in-plane flexing). In FIG. 2B, the inner shaft 14 has been rotated or torqued 90 degrees from the position shown in FIG. 2A so that the section of the distal end portion 20 extending from the outer shaft 52 lies in the y-z plane while the outer shaft lies in the x-y plane (referred to as 90-degree out-of-plane flexing). In FIG. 2C, the inner shaft 14 has been rotated or torqued 180 degrees from the position shown in FIG. 2A so that the section of the distal end portion 20 extending from the outer shaft 52 lies in the x-y plane along with the outer shaft 52 (referred to as 180-degree in-plane flexing). In FIG. 2D, the inner shaft 14 has been rotated or torqued 270 degrees from the position shown in FIG. 2A so that the section of the distal end portion 20 extending from the outer shaft 52 lies in the y-z plane while the outer shaft lies in the x-y plane (referred to as 270-degree out-of-plane flexing). As can be appreciated, the distal end portion 20 of the inner shaft 14 can be rotated relative to the central axis of the outer shaft 52 to any rotational position through 360 degrees, with 1:1 correspondence between the handle 12 and distal end portion 20 of the inner shaft 14. By employing the pull-wire sleeve 28, the inner shaft 14 can be rotated to any position within the anatomy of a patient and can be maintain that position without undesirable whipping. In contrast, using an ordinary steerable catheter in place of the catheter device 10 as the inner catheter in a coaxial-steerable-catheter arrangement results in a "double banana" configuration, preventing the inner catheter from rotating relative to the outer catheter without whipping.

It should be noted that the catheter device 10 need not include an outer shaft 52. In cases where an outer shaft is not used, component 52 in FIGS. 2A-2D can represent a body vessel (e.g., an artery), which causes the inner shaft 14 to generally assume the shape of the curved pathway of the vessel. The delivery device 10 can be operated in the same way as described above such that the inner shaft 14 can be rotated or torqued relative to its central longitudinal axis to any rotational position through 360 degrees and maintained at that position.

The catheter device 10 can be used to perform any diagnostic, therapeutic, or interventional procedure where access to a target location inside the body of a patient is desired. For example, the catheter device 10 can be used, for example, to deliver and deploy a prosthetic device in the body, to deliver tools to a target location in the body, and/or to deliver or introduce drugs or other agents, to name a few exemplary uses. In particular embodiments, the catheter device 10 can be a delivery device configured to deliver a prosthetic heart valve to one of the native valves of the heart (the aortic, mitral, pulmonary, or tricuspid valves).

In one specific example, the delivery device can include an inflatable balloon that is configured to expand and deploy a plastically-expandable prosthetic heart valve. The inflatable balloon can be mounted on the distal end portion of the inner shaft 14, or alternatively, the delivery device can include a balloon mounted on a separate shaft that extends through the steerable shaft 14, as further disclosed U.S. Patent Application Publication Nos. 2013/0030519, 2009/0281619, 2008/0065011, and 2007/0005131, the disclosures of which are incorporated by reference in their entireties. Exemplary plastically-expandable prosthetic heart valves are disclosed in U.S. Patent Application Publication Nos. 2010/0036484 and 2012/0123529, which are incorporated herein by reference.

In another example, the delivery device can be used to delivery and deploy a self-expandable prosthetic heart valve (e.g., a prosthetic valve having a frame formed from a shape-memory material, such as nitinol). To deliver a self-expandable prosthetic valve, the prosthetic valve can be loaded into a delivery sheath or sleeve in a radially compressed state and advanced from the distal open end of the sheath at the target location to allow the prosthetic valve to expand to its functional size. The delivery sheath can be the distal end portion of the steerable shaft 14 or the distal end portion of another shaft that extends through the steerable shaft 14. Further details regarding a self-expandable prosthetic valve and delivery devices for a self-expandable prosthetic valve are disclosed in U.S. Patent Application Publication Nos. 2010/0049313 and 2012/0239142, which are incorporated herein by reference.

The delivery device can be introduced and advanced through the patient's vasculature using any known delivery technique. In a transfemoral procedure, the delivery device can be inserted through a femoral artery and the aorta to access the heart (typically, but not exclusively used for aortic valve replacement). The delivery device is particularly useful for delivering a prosthetic valve to the native aortic valve as the torqueability of the delivery device allows for precise positioning of the prosthetic valve at the target site despite the tortuous pathway the delivery device must follow to reach the heart. In a transventricular procedure, the delivery device can be inserted through a surgical incision made on the bare spot on the lower anterior ventricle wall (typically, but not exclusively used for aortic or mitral valve replacement). In a transatrial procedure, the delivery device can be inserted through a surgical incision made in the wall of the left or right atrium. In a transaortic procedure, the delivery device can be inserted through a surgical incision made in the ascending aorta and advanced toward the heart (typically, but not exclusively used for aortic valve replacement). In a transeptal procedure, the delivery device can be advanced to the right atrium, such as via a femoral vein, and through the septum separating the right and left ventricles (used for aortic or mitral valve replacement).

Figure 6:
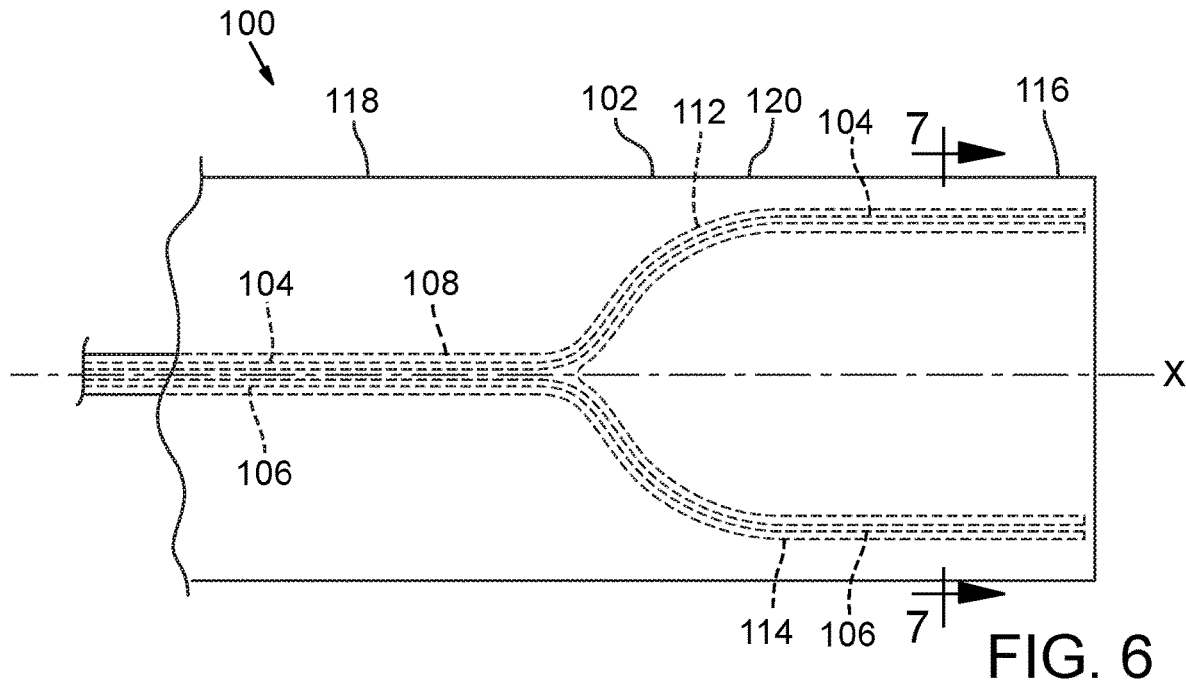
FIG. 6 is a schematic side view of a distal end portion of a catheter device, according to another embodiment, having two pull wires which extend through a central proximal lumen and two distal lumens.
Figure 7:
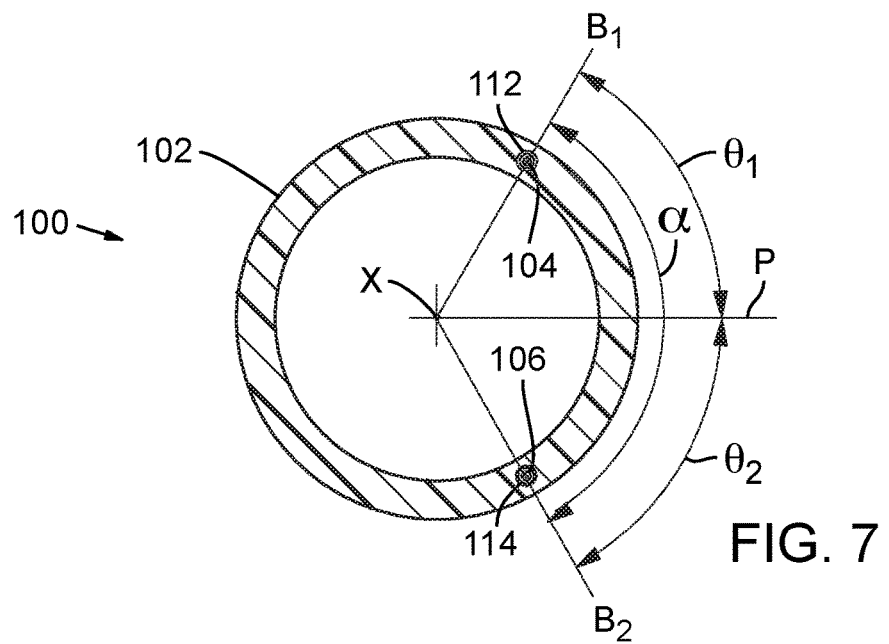
FIG. 7 is a cross-sectional view of the catheter device of FIG. 6, taken along line 7-7 of FIG. 6.
Figure 8:
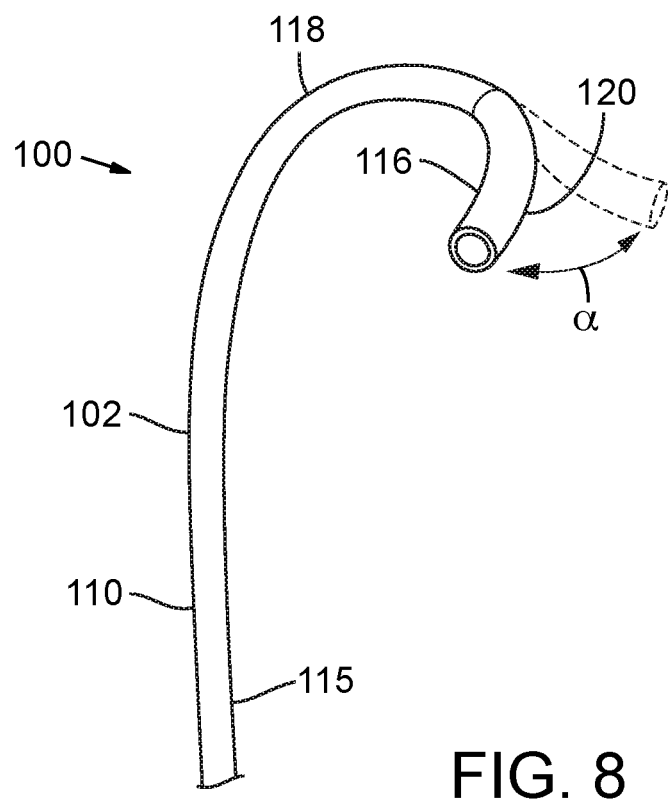
FIG. 8 is a perspective view of the catheter device of FIG. 6, showing the ability of the distal tip portion to flex at various angles within a range of flexion (a) of the distal tip portion.

FIGS. 6 and 7 show a catheter device 100, according to another embodiment. The catheter device 100 in the illustrated embodiment comprises a first pull wire 104, a second pull wire 106, and a shaft 102 having a proximal portion 115 (FIG. 8) and a steerable distal portion 116. The distal portion 116 can be relatively more flexible than the proximal portion 115, as previously described in connection with the catheter device 10 of FIG. 1. The proximal portion 115 can be coupled to a handle (not shown) that can have one or more adjustment mechanisms for increasing and decreasing tension in the pull wires 104, 106. In particular embodiments, the catheter device 100 has two adjustment mechanisms, each of which is connected to a respective pull wire 104, 106.

The main body 110 can further comprise a main pull-wire lumen 108 extending parallel to a central axis X of the shaft through the proximal portion 115 and through a proximal section 118 of the distal portion 116. The main pull-wire lumen 108 can then split into a first distal pull-wire lumen 112 and a second distal pull-wire lumen 114 that diverge away from each other and then extend generally parallel to each other at angularly spaced locations through a distal section 120 of the distal portion 116 of shaft. The pull wires 104, 106 can thus extend through the main pull-wire lumen 108 over the proximal portion 115 and the proximal section 118 of the distal portion 116 of the shaft. The first and second pull wires 104, 106 then part ways to extend into the first distal pull-wire lumen 112 and the second distal pull-wire lumen 114, respectively, over the distal section 120 of the distal portion 116.

FIG. 7 shows the angular positioning of the two distal pull-wire lumens 112, 114 (and thus the pull wires 104, 106) along an arc defined by the side wall of the shaft 102. In the illustrated embodiment, the two distal pull-wire lumens 112, 114 are disposed within the side wall of the shaft 102. In other embodiments, the distal pull-wire lumens 112, 114 have a different location, for example, adjacent to an interior of the side wall or adjacent to an exterior of the side wall. The first pull-wire lumen 112 can be positioned along a first axis $B_1$ extending radially from the central axis X of the shaft 102 to the first lumen 112. The second pull wire lumen 114 can be positioned along a second axis $B_2$ extending radially from the central axis X of the shaft 102 to the second lumen 114. As shown, the distal lumens 112, 114 are spaced angularly apart from one another by angle α between axes $B_1$ and $B_2$ along an arc defined by the side wall of the shaft. The angle α can be any angle greater than zero degrees and less than 180 degrees. In the embodiment shown, the angle α is about 120 degrees. This dual wire configuration allows the shaft 102 to have a primary flexing section (corresponding to the proximal section 118 of the steerable distal portion 116) and secondary flexing section (corresponding to the distal section 120 of the steerable distal portion 116). In some embodiments, a durometer of the primary flexing section 118 is about the same as, higher than, or lower than a durometer of the secondary flexing section 120 depending on a desired relative flexibility between the two sections. The primary flexing section has a lower durometer than the main shaft, which is the portion of the shaft 102 proximal of the primary flexing section in the illustrated embodiment that is substantially not steerable. In some embodiments, the main shaft has a higher durometer than the secondary flexing section, which in turn has a higher durometer than the primary flexing section.

In an alternative embodiment, the pull wires 104, 106 need not extend through a common main pull-wire lumen 108 and instead extend through separate longitudinally extending pull-wire lumens that are parallel and in close proximity to each other or without any spacing between each other along the length of the proximal portion 115 and the proximal section 118 of the distal portion, and then diverge away from each other and extend along the distal section 120 with a spacing α between the two pull-wire lumens.

When one or both pull wires 104, 106 are under tension, the primary flexing section 118 flexes or curves in a respective flexing plane P (FIG. 7). By virtue of the pull wires extending through a common pull-wire lumen (or extending through separate lumens in very close proximity to each other), tensioning either one or both pull wires is effective to adjust the curvature of the primary flexing section 118 in its respective flexing plane P. By applying differential tension to the pull wires, the secondary flexing section 120 can be caused to flex in various different directions relative to the primary flexing section 118. For example, applying the same amount of tension to each pull wire 104, 106 causes the secondary flexing section 120 to curve in the same plane P as the primary flexing section. Increasing tension in the first pull wire 104 relative to the second pull wire 106 causes the secondary flexing section 120 to curve or bend in a first direction away from the plane P of the primary flexing section 118 (shown in solid lines in FIG. 8). Likewise, increased tension in the second pull wire 106 relative to the first pull wire 104 causes the secondary flexing section 120 to curve or bend in a second direction, opposite the first direction, away from the plane P of the primary flexing section 118 (shown in phantom in FIG. 8).

In the illustrated embodiment, the secondary flexing section 120 permits a distal tip of the catheter device 100 to access a locus approximated by a portion of a surface of a sphere defined by a first range of flexion and a second range of flexion, which in some embodiments corresponds to the angular components of a spherical coordinate system. The first range has an angular width or azimuthal width α (FIG. 7) (bounded by the radial axes $B_1$ and $B_2$). The second range has polar angle with a minimum at or near the X axis (about 0°) and a maximum dependent on the durometer and length of the secondary flexing section 120 (maximally flexed state). Accordingly, tensioning pull wire 104, optionally while partially untensioning pull wire 106, flexes the secondary flexing section 102 radially outwards generally along axis $B_1$. Similarly, pull wire 106 is operable to flex the secondary flexing section 102 along axis $B_2$. By adjusting the relative tensions between the pull wires 104, 106, the distal tip of the catheter device 100 can be steered to any intermediate location or point in this space.

The secondary flexing section 120 can thus be made to flex in any radial flexing plane within angle α. The angular positioning of the lumens 112, 114 and the pull wires 104, 106 thus defines the azimuthal or first range of flexion α for the secondary flexing section 120. In the embodiment shown in, this direction of flexion can be in any plane between about −60° and about +60° relative to the primary flexing plane, wherein the 0° direction is the primary flexing plane P. Accordingly, in this case, the first range of flexion α is about 120°. In other embodiments, the angle α and the corresponding first range of flexion can vary, such as about 140° (about −70° to about +70°), about 130° (about −65° to about +65°), about 110° (about −55° to about +55°), about 100° (about −50° to about +50°), about 90° (about −45° to about +45°), about 80° (about −40° to about +40°), about 70° (about −35° to about +35°), or about 60° (about −30° to about +30°).

In other embodiments, the first range of flexion of the secondary flexing section 120 need not be symmetrical relative to the primary flexing plane P. For example, the portion of the first pull wire 104 in the first distal lumen 112 can be angularly spaced from the main pull wire lumen 108 (and the primary flexing plane P) a first angle $\theta_1$ and the portion of the second pull wire 106 in the second distal lumen 114 can be angularly spaced from the main pull wire lumen 108 (and the primary flexing plane P) a second angle $\theta_2$, wherein $\theta_1$ and $\theta_2$ are not equal to each other. In this manner, the first range of flexion of the secondary flexing section 120 encompasses the primary flexing plane P but can be adjusted to extend further on one side of the primary flexing plane P than the other.

Figure 9:
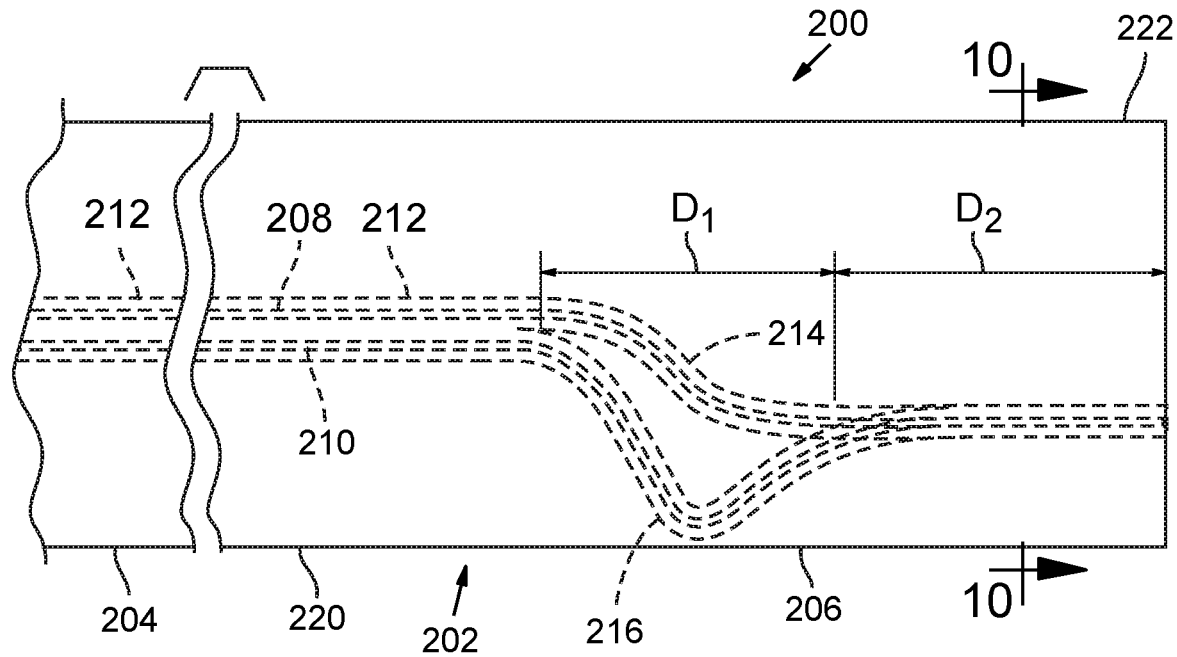
FIG. 9 is a schematic side view of a catheter device comprising two pull wires, according to another embodiment.
Figure 10:
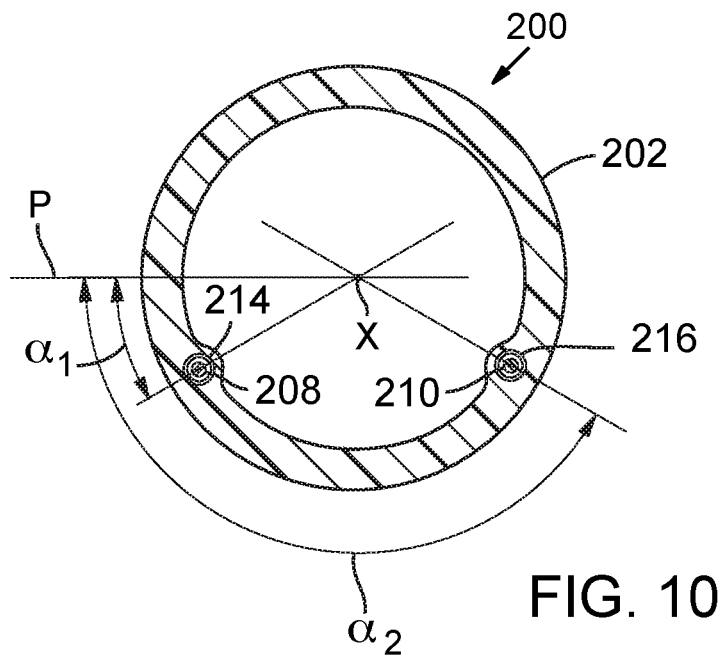
FIG. 10 is a cross-sectional view of the catheter device of FIG. 9, taken along line 10-10 of FIG. 9.
Figure 11:
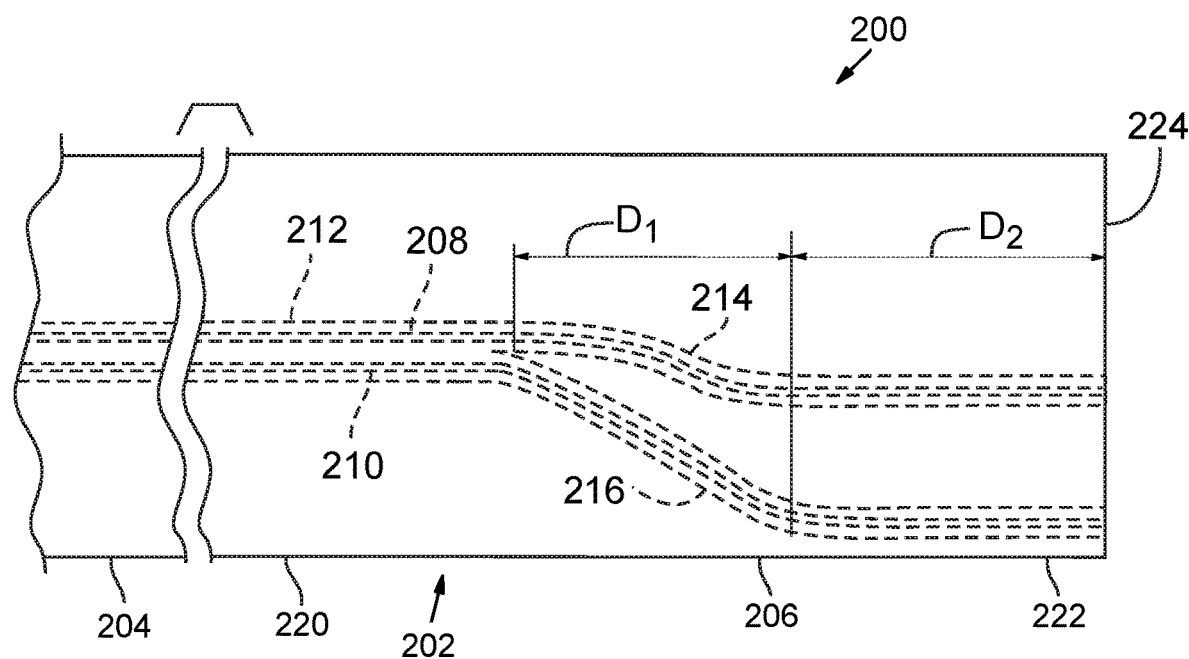
FIG. 11 is a flattened view of the catheter device of FIG. 9 with the catheter wall opened along a line opposite the main pull-wire lumen.

FIGS. 9, 10, and 11 show a catheter device 200, according to another embodiment. The catheter device 200 is similar to the catheter device 100 and can have all of the features described above in connection with the catheter device 100 except that first range of flexion of the secondary flexing section does not encompass the primary flexing section. FIG. 9 is a side view, FIG. 10 is a transverse cross-sectional view, and FIG. 11 is a flattened view with the catheter wall opened along a line opposite the main pull-wire lumen. Referring to FIGS. 9 and 11, the catheter device 200 comprises a shaft 202 having a proximal portion 204 and a distal portion 206. First and second pull wires 208, 210, respectively, extend through the proximal and distal portions of the shaft. The proximal portion 204 can be coupled to a handle (not shown) that can have one or more adjustment mechanisms for increasing and decreasing tension in the pull wires, either independently or together.

The shaft 202 can further comprise a main pull-wire lumen 212 extending parallel to a central axis X of the shaft through the proximal portion 204 and through a proximal section 220 of the distal portion 206. Some embodiments of the shaft include separate pull-wire lumens rather than a single main pull-wire lumen, as discussed above for the catheter device 100. The main pull-wire lumen 212 can then split into a first distal pull-wire lumen 214 and a second distal pull-wire lumen 216 that diverge away from each other and then extend parallel to each other at angularly spaced locations through a distal section 222 of the distal portion 206 of shaft. The pull wires 208, 210 can thus extend through the main pull-wire lumen 212 over the proximal portion 204 and the proximal section 220 of the distal portion 206 of the shaft. The first and second pull wires 208, 210 then part ways to extend into the first distal pull-wire lumen 214 and the second distal pull-wire lumen 216, respectively, over the distal section 222 of the distal portion 206. Similar to the embodiment of FIGS. 6-7, the proximal section 220 defines a primary flexing section and the distal section 222 defines a secondary flexing section. The primary flexing section 220 flexes or bends in a primary flexing plane P.

Unlike the embodiment of FIGS. 6-7, as best seen in FIGS. 9 and 11, at the distal end of the main pull-wire lumen 212, the distal pull-wire lumens 214, 216 initially extend circumferentially and longitudinally away from main pull-wire lumen 212 at different angles or pitches, over a first distance $D_1$. The distal pull-wire lumens 214, 216 then extend parallel to each other over a distance $D_2$. Due to the curvatures of the distal pull-wire lumens 214, 216, the portions of the pull wires 208, 210 extending through the distal section 222 are angularly offset to one side of the primary flexing plane P. The first pull wire 208 is angularly offset from the primary flexing plane P by a first angle $\alpha_1$ and the second pull wire 210 is angularly offset from the primary flexing plane by a second angle $\alpha_2$. Thus, the first range of flexion of the secondary flexing section 222 is between $\alpha_1$ and $\alpha_2$ relative to the primary flexing plane P. In one specific example, first range of flexion of the secondary flexing section 222 is between +30° and +150° relative to the primary flexing plane P. However, it should be understood that the angles $\alpha_1$, $\alpha_2$ can vary in different embodiments wherein $\alpha_1$ and $\alpha_2$ are any angles between zero and 180 degrees and $\alpha_2$ is greater than $\alpha_1$.

In use, tensioning one or both of the pull wires 208, 210 effectively adjusts the curvature of the primary flexing section 220 in the primary flexing plane. By applying different amounts of tension to the pull wires, the secondary flexing section 222 can be made to flex in a respective secondary flexing plane that extends at any angle relative to the primary flexing plane between $\alpha_1$ and $\alpha_2$.

Figure 12:
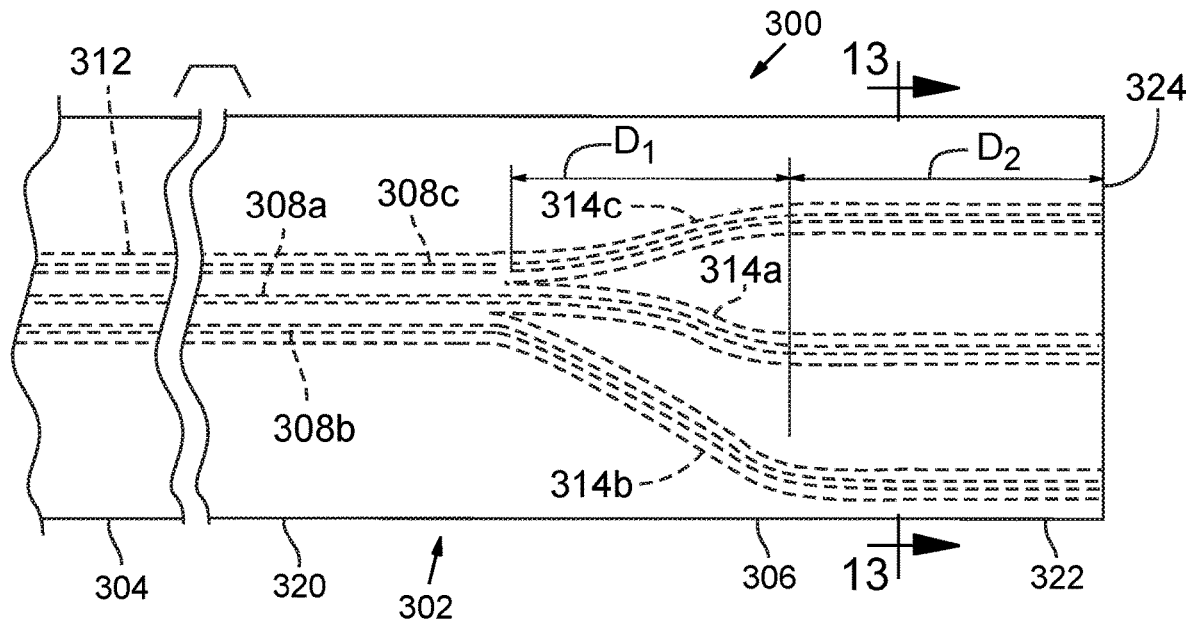
FIG. 12 is a flattened view of another embodiment of a catheter device.
Figure 13:
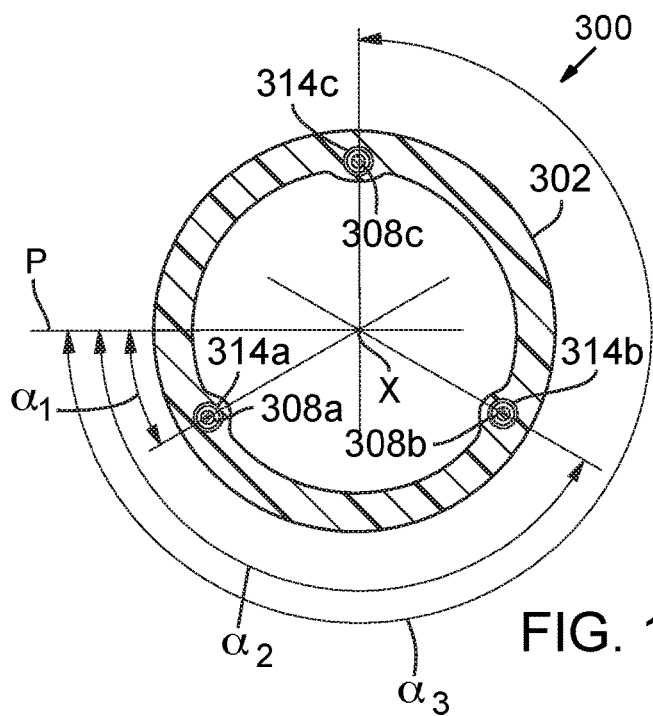
FIG. 13 is a transverse cross section of the catheter device of FIG. 12.

FIG. 12 is a flattened view and FIG. 13 is a transverse cross section of another embodiment of a catheter device 300 that is similar to the catheter devices 100 and 200, and consequently, can include any combination of features of catheter devices 100 and/or 200. Similarly to the catheter devices 100 and 200, the catheter device 300 comprises a shaft 302, a proximal portion 204, and a distal portion 206 including a primary flexing section and a secondary flexing section. A main pull-wire lumen 312 extends through a wall of the shaft 302 and proximal section 320 of the distal portion 206, parallel to a central axis X of the shaft. A first distal pull-wire lumen 314a, a second pull-wire lumen 314b, and a third pull-wire lumen 314c, diverge from the main pull-wire lumen before extending longitudinally down a distal section 322 of the distal portion 306 of the catheter device.

As shown in FIG. 13, the first pull wire 312a is offset from the primary flexing plane P by an angle $\alpha_1$, the second pull wire 312b is offset by $\alpha_2$, and the third pull wire by $\alpha_3$, where $\alpha_3 > \alpha_2 > \alpha_1$, and $\alpha_3 < 360°$. In the illustrated embodiment, the first, second, and third distal pull-wire lumens are generally equally spaced around a circumference of the distal section, for example, about 120° apart, and $\alpha_1$ is about 30°, $\alpha_2$ is about 150°, and $\alpha_3$ is about 270°. Other embodiments include other relative spacings and/or offsets for the distal pull wires and lumens, for example, where control over a particular part of a total accessible range of secondary flexing portion is of greater interest to a user.

The first, second, and third pull-wire lumens 314a, 314b, and 314c extend distally from the main pull-wire lumen and diverge circumferentially from each other over a distance $D_1$, then continue distally, generally parallel to each other over a distance $D_2$. In the illustrated embodiment, the first distal pull-wire lumen 314a extends from the main pull-wire lumen at an angle, but in other embodiments, the first pull-wire lumen extends substantially straight out of the main pull-wire lumen.

The catheter device also includes a first pull wire 308a, a second pull wire 308b, and a third pull wire 308c. The pull wires 308a, 308b, and 308c are disposed within the main pull-wire lumen 312, and within their respective distal pull-wire lumens 314a, 314b 314c. A distal end of each pull wire is secured to the wall of the catheter device at or near a distal end 324 thereof, for example, terminating at a ring at or near the distal end 324. In other embodiments, the distal ends of the pull wires are secured to the wall at a location more proximal than the distal end 324, for example, in embodiments in which the distal end 324 is not steerable. The proximal section 320 of the distal portion defines a primary flexing section, and the distal section 222 defines a secondary flexing section, which is generally coextensive with the part of the shaft 304 housing the distal pull-wire lumens in the illustrated embodiment.

As such, the illustrated embodiment of catheter device 300 is similar to the illustrated embodiment of catheter device 200 with the first and second pull wires 308a, 308b corresponding to the first and second pull wires 208, 210, respectively, and the first and second distal pull-wire lumens 314a, 314b corresponding to the first and second pull-wire lumens 214, 216, respectively. The catheter device 300 also includes the third pull wire 308c and respective third pull-wire lumen 314c, the addition of which, in combination with the first and second pull wires, increases a first range of flexion of the secondary flexing portion to a full 360° around the central axis X in the illustrated embodiment.

As discussed above, some embodiments of the catheter device 300 have a different configuration of the pull wires, for example, unequal circumferential spacing. Some of those configurations will not have an effective first range of flexion of 360° around the axis X, but instead will have a reduced effective first range of flexion, for example, about 240°, or about 180°.

In general, deflecting the second flexing section is more controllable when the pair of pull wires controlling that portion of the deflection are disposed closer together circumferentially (e.g., a smaller angular width). As such, there is a tradeoff between controllability and range. Accordingly, some embodiments of the catheter device 300 include greater than 3 pull wires, embodiments of which provide improved controllability in combination with up to a 360° first range of flexion.

General Considerations

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and subcombinations with one another. The methods, devices, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B", "C", "A and B", "A and C", "B and C", or "A, B, and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A steerable catheter device, comprising:
a shaft having a proximal portion and a distal portion; and
first and second pull wires having respective proximal portions and respective distal portions, the proximal portions of the first and second pull wires extending through the proximal portion of the shaft in close proximity to each other, and the distal portions of the first and second pull wires extending through the distal portion of the shaft in close proximity to each other over a first distance defining a primary flexing section, diverging away from each other over a second distance, and then extending parallel to each other at angularly spaced locations over a third distance defining a secondary flexing section;

wherein greater tension applied to the first pull wire than the second pull wire is effective to flex the primary flexing section in a primary flexing plane (P) and flex the secondary flexing section in a first direction away from the flexing plane (P), and wherein greater tension applied to the second pull wire than the first pull wire is effective to flex the primary flexing section in the flexing plane (P) and flex the secondary flexing section in a second direction opposite the first direction and away from the flexing plane (P).

2. The catheter device of claim 1, wherein the shaft comprising a main pull-wire lumen extending through the proximal portion of the shaft and first and second distal pull-wire lumens extending from the main pull-wire lumen, the distal pull-wire lumens diverging away from each other and then extending parallel to each other at angularly spaced locations toward a distal end of the shaft, the first pull wire extending through the main pull-wire lumen and the first distal pull-wire lumen, and the second pull wire extending through the main pull-wire lumen and the second distal pull-wire lumen.

3. The catheter device of claim 1, wherein the distal portions of the first and second pull wires are angularly spaced apart from each other at an angle of less than 180 degrees in the secondary flexing section.

4. The catheter device of claim 1, wherein the distal portions of the first and second pull wires are angularly spaced apart from each other at an angle of about 120 degrees in the secondary flexing section.

5. The catheter device of claim 1, wherein the range of flexion of the distal portion of the shaft is equal to the angular spacing between the first and second pull wires in the secondary flexing section.

6. The catheter device of claim 1, wherein the first and second pull wires are configured such that when increased tension is placed on the first pull wire, relative to tension placed on the second pull wire, the curvature of the primary flexing section is adjusted in a first plane and the curvature of the secondary flexing section is adjusted to extend away from the first plane.

7. The catheter device of claim 6, wherein the first and second pull wires are equally angularly spaced from the first plane within the secondary flexing section.

8. The catheter device of claim 6, wherein first pull wire is angularly spaced from the first plane by a first angle within the secondary flexing section and the second pull wire is angularly spaced from the first plane by a second angle that is different than the first angle within the secondary flexing section.

9. The catheter device of claim 1, wherein the distal portion of the shaft has a lower durometer than the proximal portion of the shaft.

10. The catheter device of claim 9, wherein the primary flexing section has a greater durometer than the secondary flexing section.

11. The catheter device of claim 1, wherein the distal portions of the first and second pull wires extend circumferentially and longitudinally away from the proximal portions of the first and second pull wires, respectively, at different pitches over the second distance.

12. A steerable catheter device, comprising:
a shaft having a proximal portion and a distal portion; and
first and second pull wires having respective proximal portions and respective distal portions, the proximal portions of the first and second pull wires extending through the proximal portion of the shaft, and the distal portions of the first and second pull wires extending through the distal portion of the shaft over a first distance defining a primary flexing section, diverging away from each other over a second distance, and then extending at angularly spaced locations over a third distance defining a secondary flexing section such that an angular spacing between the first and second pull wires is greater in the secondary flexing section than in the primary flexing section;

wherein greater tension applied to the first pull wire than the second pull wire is effective to flex the primary flexing section relative to the proximal portion of the shaft in a first flexing plane and to flex the secondary flexing section relative to the primary flexing section in a first direction away from the first flexing plane in a second flexing plane on a first side of the first flexing plane;

wherein greater tension applied to the second pull wire than the first pull wire is effective to flex the primary flexing section relative to the proximal portion of the shaft in the first flexing plane and to flex the secondary flexing section relative to the primary flexing section in a second direction away from the first flexing plane in a third flexing plane on a second side of the first flexing plane.

13. The catheter device of claim 12, wherein the shaft comprising a main pull-wire lumen extending through the proximal portion of the shaft and first and second distal pull-wire lumens extending from the main pull-wire lumen, the distal pull-wire lumens diverging away from each other and then extending at angularly spaced locations toward a distal end of the shaft, the first pull wire extending through the main pull-wire lumen and the first distal pull-wire lumen, and the second pull wire extending through the main pull-wire lumen and the second distal pull-wire lumen.

14. The catheter device of claim 12, wherein the first and second pull wires are configured such that equal tension applied to the first and second pull wires is effective to flex the secondary flexing section within the first flexing plane.

15. The catheter device of claim 12, wherein the first and second pull wires are equally angularly spaced from the first flexing plane within the secondary flexing section.

16. The catheter device of claim 12, wherein first pull wire is angularly spaced from the first flexing plane by a first angle within the secondary flexing section and the second pull wire is angularly spaced from the first flexing plane by a second angle that is different than the first angle within the secondary flexing section.

17. The catheter device of claim 12, wherein the distal portions of the first and second pull wires extend circumferentially and longitudinally away from the proximal portions of the first and second pull wires, respectively, at different pitches over the second distance.

18. A steerable catheter device, comprising:
a shaft having a proximal portion and a distal portion; and
first and second pull wires having respective proximal portions and respective distal portions, the proximal portions of the first and second pull wires extending through the proximal portion of the shaft, and the distal portions of the first and second pull wires extending through a primary flexing section of the distal portion of the shaft, then through a transition section of the distal portion of the shaft in which the first and second pull wires extend circumferentially and longitudinally away from the primary flexing section, and then through a secondary flexing section of the distal portion of the shaft such that an angular spacing between the first and second pull wires is greater in the secondary flexing section than in the primary flexing section;

wherein greater tension applied to the first pull wire than the second pull wire is effective to flex the primary flexing section relative to the proximal portion of the shaft in a first flexing plane and to flex the secondary flexing section relative to the primary flexing section in a first direction away from the first flexing plane;

wherein greater tension applied to the second pull wire than the first pull wire is effective to flex the primary flexing section relative to the proximal portion of the shaft in the first flexing plane and to flex the secondary flexing section relative to the primary flexing section in a second direction away from the first flexing plane;

wherein differential tensioning of the first and second pull wires allows the secondary flexing section to flex in any flexing plane within an angle ($\alpha$) relative to the first flexing plane equal to the angular spacing between the first and second pull wires, wherein the angle ($\alpha$) is measured between a first radial axis (B1) and a second radial axis (B2), and wherein the first radial axis (B1) extends from the first pull wire to a central axis of the shaft, and the second radial axis (B2) extends from the second pull wire to the central axis of the shaft.

19. The catheter device of claim 18, wherein differential tensioning of the first and second pull wires produces movement of the secondary flexing section along a locus approximating a portion of a surface of a sphere.

* * * * *